United States Patent
Aum et al.

(10) Patent No.: US 12,136,218 B2
(45) Date of Patent: Nov. 5, 2024

(54) METHOD AND SYSTEM FOR PREDICTING EXPRESSION OF BIOMARKER FROM MEDICAL IMAGE

(71) Applicant: LUNIT INC., Seoul (KR)

(72) Inventors: Jae Hong Aum, Seoul (KR); Chanyoung Ock, Seoul (KR); Donggeun Yoo, Seoul (KR)

(73) Assignee: LUNIT INC., Seoul (KR)

( * ) Notice: Subject to any disclaimer, the term of this patent is extended or adjusted under 35 U.S.C. 154(b) by 356 days.

(21) Appl. No.: 17/502,260

(22) Filed: Oct. 15, 2021

(65) Prior Publication Data

US 2022/0036558 A1 Feb. 3, 2022

Related U.S. Application Data

(63) Continuation of application No. PCT/KR2021/002728, filed on Mar. 5, 2021.

(30) Foreign Application Priority Data

Mar. 6, 2020 (KR) .................. 10-2020-0028686

(51) Int. Cl.
*G06T 7/00* (2017.01)
*A61B 5/00* (2006.01)
(Continued)

(52) U.S. Cl.
CPC .......... *G06T 7/0016* (2013.01); *A61B 5/4887* (2013.01); *A61B 5/7275* (2013.01);
(Continued)

(58) Field of Classification Search
CPC ............ G06T 7/0016; G06T 7/11; G06T 2207/20081; G06T 2207/20132; G06T 2207/30096; G16H 30/20; G16H 50/30; A61B 5/4887; A61B 5/7275; A61B 2576/02
See application file for complete search history.

(56) References Cited

U.S. PATENT DOCUMENTS

2013/0170728 A1* 7/2013 Sarachan ............ G06T 7/11
702/19
2017/0236271 A1 8/2017 Kim et al.
(Continued)

FOREIGN PATENT DOCUMENTS

| CN | 110796672 A | 2/2020 |
|---|---|---|
| JP | 2010531155 A | 9/2010 |

(Continued)

OTHER PUBLICATIONS

Translation of the International Search Report of PCT/KR2021/002728 dated Jun. 18, 2021.
(Continued)

*Primary Examiner* — Khai M Nguyen
(74) *Attorney, Agent, or Firm* — Sughrue Mion, PLLC

(57) ABSTRACT

The present disclosure relates to a method for predicting biomarker expression from a medical image. The method for predicting biomarker expression includes receiving a medical image, and outputting indices of biomarker expression for the at least one lesion included in the medical image by using a first machine learning model.

20 Claims, 15 Drawing Sheets

(51) Int. Cl.
  *G06T 7/11*    (2017.01)
  *G16H 30/20*   (2018.01)
  *G16H 50/30*   (2018.01)

(52) U.S. Cl.
  CPC .............. *G06T 7/11* (2017.01); *G16H 30/20* (2018.01); *G16H 50/30* (2018.01); *A61B 2576/02* (2013.01); *G06T 2207/20081* (2013.01); *G06T 2207/20132* (2013.01); *G06T 2207/30096* (2013.01)

(56) References Cited

U.S. PATENT DOCUMENTS

| 2020/0258223 | A1  | 8/2020  | Yip et al. |            |
|---|---|---|---|---|
| 2020/0372281 | A1* | 11/2020 | Ganeshan | G06V 10/443 |
| 2021/0073986 | A1* | 3/2021  | Kapur    | G06T 7/11   |
| 2021/0090694 | A1* | 3/2021  | Colley   | G16H 15/00  |
| 2021/0193323 | A1* | 6/2021  | Jain     | G16H 50/30  |
| 2022/0000351 | A1* | 1/2022  | Yamada   | G16H 30/40  |

FOREIGN PATENT DOCUMENTS

| KR | 1020080021723 A | 3/2008 |
|---|---|---|
| KR | 1020180040287 A | 4/2018 |
| KR | 1020190046471 A | 5/2019 |
| KR | 1020190113351 A | 10/2019 |
| WO | 2019/103912 A2  | 5/2019 |

OTHER PUBLICATIONS

Mwen Xu, et al., "Deep Learning Predicts Lung Cancer Treatment Response from Serial Medical Imaging," Clinical Cancer Research, vol. 25, No. 11, Jun. 1, 2019, pp. 3266-3275 (10 pages total).

* cited by examiner

510

520

610

730

720

710

810

820

METHOD AND SYSTEM FOR PREDICTING EXPRESSION OF BIOMARKER FROM MEDICAL IMAGE

CROSS-REFERENCE TO RELATED APPLICATIONS

This application is a continuation of International Patent Application No. PCT/KR2021/002728 filed on Mar. 5, 2021, which claims priority to Korean Patent Application No. 10-2020-0028686 filed on Mar. 6, 2020, the entire contents of which are herein incorporated by reference.

BACKGROUND

Technical Field

The present disclosure relates to a method and a system for predicting biomarker expression, and specifically, to a method and a system for predicting biomarker expression for at least one lesion included in a medical image.

Background Art

In order to confirm cancer and suggest an appropriate treatment, it is necessary to collect cancer tissue from a patient and precisely analyze the collected cancer tissue. When collecting cancer tissue from a patient, in order to suggest an appropriate treatment to the patient, it is necessary to collect representative lesions among cancer lesions. In general, in such a clinical trial, a lesion in patient's body is selected under the subjective determination of a clinician. Specifically, since the clinicians base their determination on criteria such as the size and location of the lesion, which can be influenced by their own subjective criteria or determination, it may not be highly likely that lesions representing all of the patient's lesions will be collected.

In addition, when collecting lesions in the traditional clinical trials, tissue collection is performed several times until the results from the patient show that a specific drug would be effective when used. Moreover, unnecessary tissue collection process may act as a factor that delays the patient's treatment time, adversely affecting the patient's survival. Furthermore, the act of collecting tissue itself may threaten the patient's health and be a physically demanding process.

SUMMARY

Technical Problem

In order to solve the problems described above, the present disclosure provides a method, a computer program stored in a recording medium, and an apparatus (system) for predicting expression of a biomarker.

Technical Solution

The present disclosure may be implemented in a variety of ways, including a method, a device (system) or a computer program stored in a readable storage medium.

According to an embodiment, a method, performed by at least one processor, for predicting biomarker expression from a medical image include receiving a medical image, and outputting indices of biomarker expression for the at least one lesion included in the medical image by using a first machine learning model.

According to an embodiment, the outputting the indices of biomarker expression may include extracting regions for the at least one lesion from the received medical image, and cropping the extracted regions for the at least one lesion from the medical images to generate partial images.

According to an embodiment, the outputting the indices of biomarker expression may include inputting the generated partial images to the first machine learning model to output the indices of biomarker expression for the at least one lesion.

According to an embodiment, the outputting the indices of biomarker expression may include inputting the received medical image and the generated partial images to the first machine learning model to output the indices of biomarker expression for the at least one lesion.

According to an embodiment, the method may further include determining segmentation information of the at least one lesion included in the medical image. The outputting the indices of biomarker expression may include inputting the determined segmentation information of the at least one lesion and the generated partial images to the first machine learning model to output the indices of biomarker expression for the at least one lesion included in the medical image.

According to an embodiment, the method may include acquiring an index of biomarker expression for a lesion different from the at least one lesion in the medical image. The outputting the indices of biomarker expression may include inputting the acquired index of biomarker expression of the different lesion and the generated partial images to the first machine learning model to output the indices of biomarker expression for the at least one lesion included in the medical image.

According to an embodiment, the receiving the medical image may include receiving a first medical image and a second medical image captured at a point in time different from the first medical image. The outputting the indices of biomarker expression may include extracting regions for the at least one lesion from each of the first medical image and the second medical image, and inputting the regions for the at least one lesion extracted from the first medical image and the regions for the at least one lesion extracted from the second medical image to the first machine learning model to output the indices of biomarker expression for the at least one lesion.

According to an embodiment, the method may further include inputting the output indices of biomarker expression into a third machine learning model to output information associated with tissue collection for the at least one lesion.

According to an embodiment, the at least one lesion included in the medical image may include a plurality of lesions included in the medical image. The outputting the information associated with tissue collection for the at least one lesion may include outputting information on a priority of tissue collection for the plurality of lesions.

According to an embodiment, the method may further include acquiring reference information on tissue collection associated with the medical image. The outputting the information on the priority of tissue collection for the plurality of lesions may include inputting the output indices of biomarker expression and the acquired reference information on tissue collection into the third machine learning model to output the information on a priority of tissue collection for the plurality of lesions.

An information processing system according to another embodiment of the present disclosure is provided, which may include a memory storing one or more instructions, and a processor configured to execute the stored one or more instructions to receive a medical image and output indices of biomarker expression for at least one lesion included in the medical image by using a first machine learning model.

Advantageous Effects

According to some embodiments of the present disclosure, a user (e.g., a doctor, and the like) can check the possibility of expression of the biomarker in the at least one lesion included in the medical image, and determine an optimal lesion to perform the tissue collection.

According to some embodiments of the present disclosure, when provided with the information on the lesion determined as described above, the doctor can directly perform tissue collection on the patient without having to go through unnecessary tissue collection processes, thus eliminating the discomfort that the patient may feel, and also without significantly affecting the patient's probability of survival.

According to some embodiments of the present disclosure, the user can check output indices of biomarker expression and then start collecting tissues from a lesion with a highest probability of biomarker expression, thereby minimizing the burden on the patient for tissue collection.

According to some embodiments of the present disclosure, the processor may use not only the first medical image but also the second medical image captured at a point in time different from the first medical image to predict indices of biomarker expression in the first medical image, thereby outputting a more accurate prediction result for the indices of biomarker expression.

According to some embodiments of the present disclosure, the processor can predict the indices of biomarker expression in the medical image by using the indices of the expression and/or the actual amount of the expression of the biomarker of the lesion different from the at least one lesion, thereby outputting a more accurate prediction result for the indices of biomarker expression.

According to some embodiments of the present disclosure, the first machine learning model can more accurately predict and output the indices of biomarker expression by utilizing not only the at least one image but also at least one piece of additional information.

According to some embodiments of the present disclosure, the first machine learning model can further utilize the feature of not only the medical images, but also each of the plurality of partial images, thereby more accurately predicting and outputting the indices of biomarker expression.

According to some embodiments of the present disclosure, the user can efficiently determine a lesion to collect the tissues, among the patient's lesions by using the information associated with tissue collection.

According to some embodiments of the present disclosure, the user can easily determine which lesion of the lesions included in the medical image is to be preferentially examined in order to help the treatment of the patient.

The effects of the present disclosure are not limited to the effects described above, and other effects not mentioned will be able to be clearly understood by those of ordinary skill in the art (referred to as "those skilled in the art") from the description of the claims.

BRIEF DESCRIPTION OF THE DRAWING

The above and other objects, features and advantages of the present disclosure will become more apparent to those of ordinary skill in the art by describing in detail exemplary embodiments thereof with reference to the accompanying drawing.

DETAILED DESCRIPTION

Figure 1:
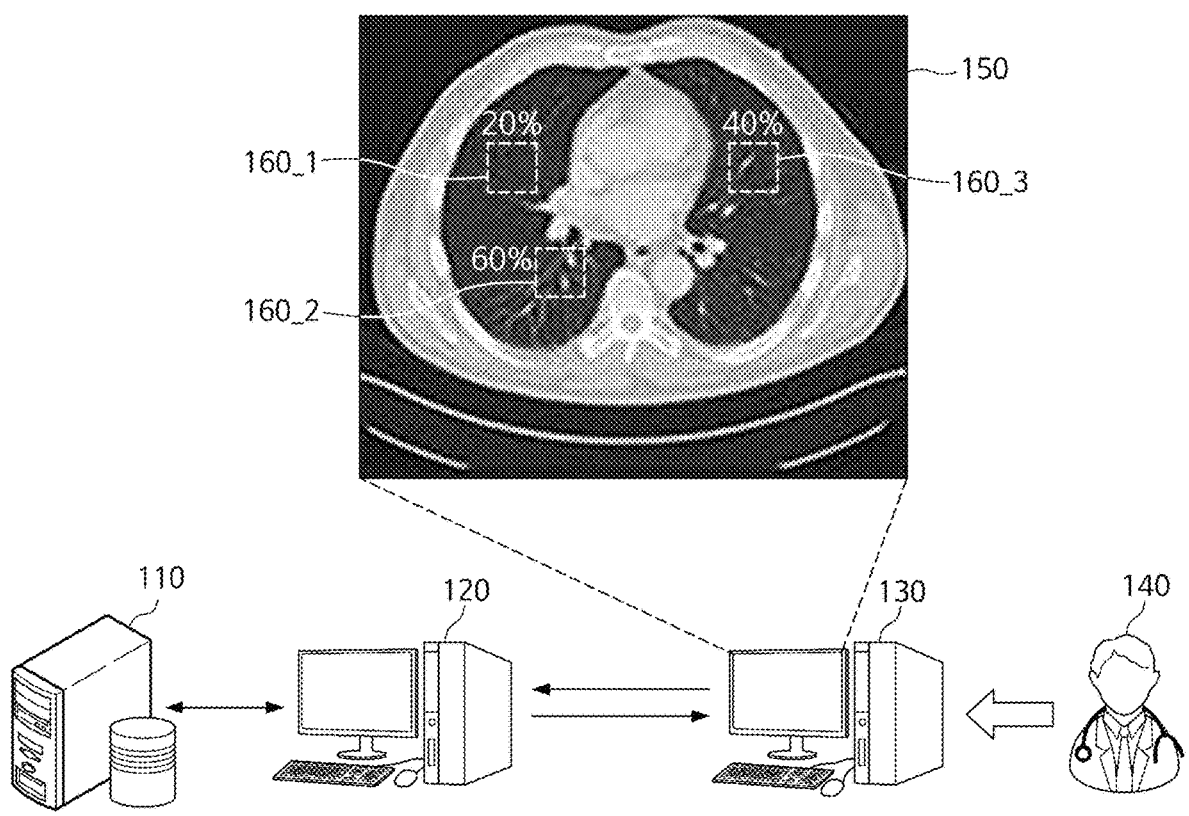
FIG. 1 is an exemplary configuration diagram illustrating an information processing system for providing indices of biomarker expression according to an embodiment.

Hereinafter, specific details for the practice of the present disclosure will be described in detail with reference to the accompanying drawings. However, in the following description, detailed descriptions of well-known functions or configurations will be omitted when it may make the subject matter of the present disclosure rather unclear.

In the accompanying drawings, the same or corresponding elements are assigned the same reference numerals. In addition, in the following description of the embodiments, duplicate descriptions of the same or corresponding components may be omitted. However, even if descriptions of components are omitted, it is not intended that such components are not included in any embodiment.

Advantages and features of the disclosed embodiments and methods of accomplishing the same will be apparent by referring to embodiments described below in connection with the accompanying drawings. However, the present disclosure is not limited to the embodiments disclosed below, and may be implemented in various different forms, and the present embodiments are merely provided to make the present disclosure complete, and to fully disclose the scope of the invention to those skilled in the art to which the present disclosure pertains.

The terms used herein will be briefly described prior to describing the disclosed embodiments in detail. The terms used herein have been selected as general terms which are widely used at present in consideration of the functions of the present disclosure, and this may be altered according to the intent of an operator skilled in the art, conventional practice, or introduction of new technology. In addition, in a specific case, the term may be arbitrarily selected by the applicant, and the meaning of the term will be described in detail in a corresponding description of the embodiments. Therefore, the terms used in the present disclosure should be defined based on the meaning of the terms and the overall content of the present disclosure rather than a simple name of each of the terms.

As used herein, the singular forms "a," "an," and "the" are intended to include the plural forms as well, unless the context clearly indicates the singular forms. Further, the plural forms are intended to include the singular forms as well, unless the context clearly indicates the plural forms. Further, throughout the description, when a portion is stated as "comprising (including)" a component, it intends to mean that the portion may additionally comprise (or include or have) another component, rather than excluding the same, unless specified to the contrary.

Further, the term "module" or "unit" used herein refers to a software or hardware component, and "module" or "unit" performs certain roles. However, the meaning of the "module" or "unit" is not limited to software or hardware. The "module" or "unit" may be configured to be in an addressable storage medium or configured to reproduce one or more processors. Accordingly, as an example, the "module" or "unit" may include components such as software components, object-oriented software components, class components, and task components, and at least one of processes, functions, attributes, procedures, subroutines, program code segments of program code, drivers, firmware, micro-codes, circuits, data, database, data structures, tables, arrays, and variables. Furthermore, functions provided in the components and the "modules" or "units" may be combined into a smaller number of components and "modules" or "units", or further divided into additional components and "modules" or "units."

According to an embodiment, the "module" or "unit" may be implemented as a processor and a memory. The "processor" should be interpreted broadly to encompass a general-purpose processor, a central processing unit (CPU), a microprocessor, a digital signal processor (DSP), a controller, a microcontroller, a state machine, and so forth. Under some circumstances, the "processor" may refer to an application-specific integrated circuit (ASIC), a programmable logic device (PLD), a field-programmable gate array (FPGA), and so on. The "processor" may refer to a combination of processing devices, e.g., a combination of a DSP and a microprocessor, a plurality of microprocessors, one or more microprocessors in conjunction with a DSP core, or any other combination of such configurations. In addition, the "memory" should be interpreted broadly to encompass any electronic component that is capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, and so on. The memory is said to be in electronic communication with a processor if the processor can read information from and/or write information to the memory. The memory integrated with the processor is in electronic communication with the processor.

In the present disclosure, the "system" may refer to at least one of a server device and a cloud device, but not limited thereto. For example, the system may include one or more server devices. As another example, the system may include one or more cloud devices. As another example, the system may be configured together with both a server device and a cloud device and operated.

In the present disclosure, the "machine learning model" may include any model that is used for inferring an answer to a given input. According to an embodiment, the machine learning model may include an artificial neural network model including an input layer (layer), a plurality of hidden layers, and output layers. In an example, each layer may include a plurality of nodes. The present disclosure describes a plurality of machine learning models such as a first machine learning model, a second machine learning model, a third machine learning model, and the like as separate machine learning models, but is not limited thereto, and some or all of the plurality of machine learning models may be implemented as one machine learning model. In addition, in the present disclosure, the machine learning model may refer to an artificial neural network model, and the artificial neural network model may refer to the machine learning model.

In the present disclosure, a "display" may refer to any display device associated with a computing device, and for example, it may refer to any display device that is controlled by the computing device, or that can display any information/data provided from the computing device.

In the present disclosure, "each of a plurality of A" may refer to each of all components included in the plurality of A, or may refer to each of some of the components included in a plurality of A.

In the present disclosure, a "biomarker" refers to an index that can indicate changes in the body using proteins, DNA, RNA, metabolites, and the like, and may include, for example, PD-L1, EGFR, DCIS, ALK, ER, HER2, VEGF, and the like, but is not limited thereto. For example, the biomarker may be a preset biomarker or a biomarker selected or set by any machine learning model. In addition, an "index of biomarker expression" refers to a numerical representation of an index that predicts a level of expression and/or a possibility of expression, and the like of a biomarker for each lesion, and may be output in the form of an amount of expression of the biomarker, an expression level, and the like.

In the present disclosure, a "medical image" may refer to any image, picture, and the like associated with the medical field. In addition, the medical image may refer to an image or a picture obtained by capturing at least a part of a patient's body, and may include a 2D image, a 3D image, a synthetic image, and the like, captured in the form of Computed Tomography (CT), Magnetic Resonance Imaging (MRI), Position Emission Tomography (PET), Single Photon Emission CT (SPECT), Digital Breast Tomosynthesis (DBT), and the like, for example.

In the present disclosure, "cropping" may refer to a process of generating partial images or pictures by cutting and selecting at least partial regions of an image, a picture, and the like. In addition, in computer graphics, the cropping may refer to a process of removing an outer area of a computer graphic to change the aspect ratio, to make a specific region stand out, or to improve the framing. For example, the cropping may include 2D cropping using 2D computer graphics, 3D cropping using 3D computer graphics, and the like.

In the present disclosure, "instructions" may refer to one or more instructions grouped based on functions, which are the components of a computer program and executed by the processor.

FIG. 1 is an exemplary configuration diagram illustrating an information processing system 120 for providing indices of biomarker expression according to an embodiment. As illustrated, the information processing system 120 may be configured so as to be communicatively connected to each of a user terminal 130 and a storage system 110. While FIG. 1 illustrates one user terminal 130, the present disclosure is not limited thereto, and in an exemplary configuration, a plurality of user terminals 130 may be connected to the information processing system 120 for communication. In addition, while the information processing system 120 is shown as one computing device in FIG. 1, the present disclosure is not limited thereto, and the information processing system 120 may be configured to process information and/or data in a distributed manner through a plurality of computing devices. In addition, while the storage system 110 is shown as a single device in FIG. 1, the present disclosure is not limited thereto, and the system may be configured with a plurality of storage devices or as a system that supports a cloud. In addition, in FIG. 1, each of the components of the system for providing indices of biomarker expression represents functional elements that are functionally classified, and in an actual physical environment, a plurality of components may be implemented in an integrated form.

The information processing system 120 and/or the user terminal 130 are any computing devices that are used to provide information on the indices of biomarker expression included in the medical image. In an example, the computing device may refer to any type of device equipped with a computing function, and may be a notebook, a desktop, a laptop, a tablet computer, a server, a cloud system, and the like, for example, but is not limited thereto. The information processing system 120 may output a medical image 150 to a display device of the user terminal 130 to provide it to a user 140. In this case, the information processing system 120 may provide the image including indices 160_1, 160_2, and 160_3 of biomarker expression for at least one lesion included in the medical image 150 to the user 140 through the user terminal 130.

According to an embodiment, the information processing system 120 may receive the medical image 150. In this case, the medical image 150 may refer to any image, picture, and the like associated with the medical field, and may include a 2D image, a 3D image, a synthetic image, and the like of Computed Tomography (CT), Magnetic Resonance Imaging (MRI), Position Emission Tomography (PET), Single Photon Emission CT (SPECT), Digital Breast Tomosynthesis (DBT), and the like, for example. Such a medical image 150 may be directly captured by a device associated with the information processing system 120, or may be received from an external system (e.g., the user terminal 130, the storage system 110, and the like).

Then, the information processing system 120 may output the indices of biomarker expression for the at least one lesion included in the medical image by using the first machine learning model. For example, the information processing system 120 may predict the indices 160_1, 160_2, and 160_3 of expression of a specific biomarker for three lesions. In another example, the information processing system 120 may also predict indices of expression of each of a plurality of biomarkers for the at least one lesion. The "biomarker" herein refers to an index that can indicate changes in the body using proteins, DNA, RNA, metabolites, and the like, and may include, for example, PD-L1, EGFR, DCIS, ALK, ER, HER2, VEGF, and the like, but is not limited thereto. In addition, the indices 160_1, 160_2, and 160_3 of biomarker expression represent the levels of expression and/or the possibility of expression, and the like of the biomarker for each lesion, and may be output in the form of an amount of expression of the biomarker, an expression level, and the like.

In order to output the indices 160_1, 160_2, and 160_3 of biomarker expression for the lesion included in the medical image 150, the information processing system 120 may first extract regions for the at least one lesion from the medical image 150. In this case, any algorithm and/or any machine learning model for extracting the regions for the lesion from the medical image 150 may be used. Additionally or alternatively, the information processing system 120 may receive the medical image 150 for which the region for the lesion is determined.

According to one embodiment, the user 140 may use the indices 160_1, 160_2, and 160_3 of biomarker expression output through the user terminal 130 to determine a lesion to perform tissue collection (biopsy). For example, the user 140 may select one lesion having a high probability of biomarker expression among various lesions included in the medical image 150 and perform tissue collection for the lesion. Additionally or alternatively, the information processing system 120 may output information on a priority of tissue collection for a plurality of lesions. In this case, the user 140 may select one lesion having a highest priority of tissue collection and perform the tissue collection for the lesion. With such a configuration, the user 140 may check the possibility of expression of the biomarker in the at least one lesion included in the medical image 150, and determine an optimal lesion to perform the tissue collection.

The storage system 110 is a device or cloud system that stores and manages various data associated with a machine learning model for providing the indices 160_1, 160_2, and 160_3 of biomarker expression for the lesions included in the medical image 150. For efficient data management, the storage system 110 may store and manage various types of data using a database. In this case, the various data may include any data associated with the machine learning model, which may include, for example, a medical image of a patient, a medical image from which an index of biomarker expression for a specific lesion is output, a medical image at a different point in time, a medical image from which an index of biomarker expression for another lesion is output, information on biomarker, patient information, segmentation information, lesion information, and the like, but is not limited thereto. While FIG. 1 shows the information processing system 120 and the storage system 110 as separate systems, the present disclosure is not limited thereto, and they may be incorporated into one system.

Figure 2:
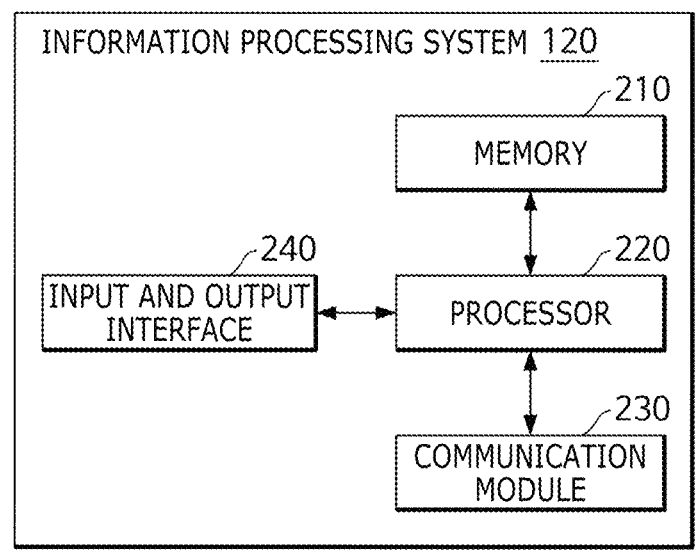
FIG. 2 is a block diagram illustrating an internal configuration of the information processing system according to an embodiment.

FIG. 2 is a block diagram illustrating an internal configuration of the information processing system 120 according to an embodiment. The information processing system 120 may include a memory 210, a processor 220, a communication module 230, and an input and output interface 240. As illustrated in FIG. 2, the information processing system 120 may be configured to communicate information and/or data through a network using the communication module 230.

The memory 210 may include any non-transitory computer-readable recording medium. According to an embodiment, the memory 210 may include a permanent mass storage device such as random access memory (RAM), read only memory (ROM), disk drive, solid state drive (SSD), flash memory, and so on. As another example, a non-destructive mass storage device such as ROM, SSD, flash memory, disk drive, and so on may be included in the information processing system 120 as a separate permanent storage device that is distinct from the memory. In addition, an operating system and at least one program code (e.g., a code installed and driven in the information processing system 120, for outputting indices of biomarker expression, outputting information associated with tissue collection, and the like) may be stored in the memory 210.

These software components may be loaded from a computer-readable recording medium separate from the memory 210. Such a separate computer-readable recording medium may include a recording medium directly connectable to the information processing system 120, and may include a computer-readable recording medium such as a floppy drive, a disk, a tape, a DVD/CD-ROM drive, a memory card, and the like, for example. As another example, the software components may be loaded into the memory 210 through the communication module 230 rather than the computer-readable recording medium. For example, at least one program may be loaded into the memory 210 based on a computer program (e.g., a program or the like for outputting indices of biomarker expression, outputting information associated with tissue collection, and the like) installed by the files provided by the developers, or by a file distribution system that distributes an installation file of an application through a communication module 230.

The processor 220 may be configured to process the commands of the computer program by performing basic arithmetic, logic, and input and output operations. The commands may be provided to a user terminal (not illustrated) or another external system by the memory 210 or the communication module 230. For example, the processor 220 may receive the medical image and output the indices of biomarker expression for the at least one lesion included in the medical image by using the first machine learning model. In this case, the processor 220 may extract regions for the at least one lesion from the received medical image and crop the extracted regions for the at least one lesion from the medical image to generate partial images. Then, the processor 220 may input the generated partial images to the first machine learning model to output indices of biomarker expression for the at least one lesion.

The communication module 230 may provide a configuration or function for the user terminal (not illustrated) and the information processing system 120 to communicate with each other through a network, and may provide a configuration or function for the information processing system 120 to communicate with an external system (e.g., a separate cloud system). For example, control signals, commands, data, and the like provided under the control of the processor 220 of the information processing system 120 may be transmitted to the user terminal and/or the external system through the communication module 230 and the network through the communication module of the user terminal and/or an external system. For example, the user terminal and/or the external system may receive from the information processing system 120 information on the determined indices of biomarker expression, and the like.

In addition, the input and output interface 240 of the information processing system 120 may be a means for interfacing with a device (not illustrated) for inputting or outputting, which may be connected to the information processing system 120 or included in the information processing system 120. In FIG. 2, the input and output interface 240 are illustrated as the components configured separately from the processor 220, but embodiments are not limited thereto, and the input and output interface 240 may be configured to be included in the processor 220. The information processing system 120 may include more components than those illustrated in FIG. 2. Meanwhile, most of the related components may not necessarily require exact illustration.

The processor 220 of the information processing system 120 may be configured to manage, process, and/or store the information and/or data received from a plurality of user terminals and/or a plurality of external systems. According to an embodiment, the processor 220 may receive the medical image from the user terminal and/or the external system. In this case, the processor 220 may output the indices of biomarker expression for the at least one lesion included in the medical image by using the first machine learning model.

Figure 3:
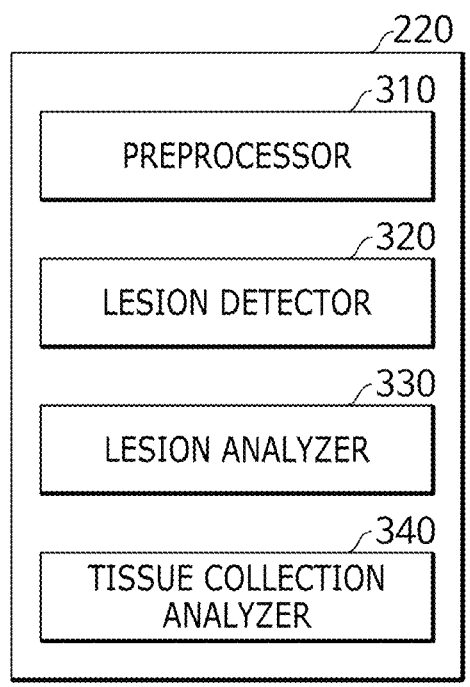
FIG. 3 is a functional block diagram illustrating an internal configuration of a processor according to an embodiment.

FIG. 3 is a functional block diagram illustrating an internal configuration of the processor 220 according to an embodiment. As illustrated, the processor 220 may include a preprocessor 310, a lesion detector 320, a lesion analyzer 330, a tissue collection analyzer 340, and the like. In this case, the processor 220 may communicate with a database of medical images and/or an external device (e.g., a user terminal or an external system), and receive a medical image required for predicting biomarker expression.

The preprocessor 310 may perform preprocessing on the received medical image. According to an embodiment, the preprocessor 310 may receive the medical image and construct the acquired image into an image of a specific dimension. For example, the preprocessor 310 may construct and/or change 2D medical image into 3D medical image, or construct and/or change 3D medical image into 2D medical image. In addition, the preprocessor 310 may perform resampling so that the length of one pixel in the received medical image is a predetermined length. That is, the preprocessor 310 may preprocess the received medical image into a form suitable for lesion detection and/or lesion analysis.

The lesion detector 320 may extract regions for the at least one lesion included in the corresponding medical image based on the received or input medical image. In this example, the region for the lesion may include at least one of a location or a size of the lesion determined to be present in the medical image. For example, the lesion detector 320 may use a predetermined algorithm and/or a machine learning model (e.g., RNN, CNN, FCNN, and the like among artificial neural network models) to extract the regions for the lesion so as to extract the lesion in the medical image, the possibility that the lesion is present, the predicted location and size of the lesion, and the like. Additionally or alternatively, at least one of the location and the size of the lesion may be selected or input by the user, and at least one of the location and the size of the lesion detected by the lesion detector 320 may be modified by the user.

According to an embodiment, the processor 220 may extract the regions for the at least one lesion from the received medical image and crop the extracted regions for the at least one lesion from the medical image to generate partial images. Furthermore, the processor 220 may adjust the size of the received medical image and the sizes of the generated partial images to a predetermined size, and concatenate the adjusted medical image and the adjusted partial images to generate the concatenated images. The medical image, the partial images, and/or the concatenated images generated as described above may be used to extract the indices of biomarker expression.

The lesion analyzer 330 may output the indices of biomarker expression for the at least one lesion included in the medical image such as 2D image, 3D image, and the like. The lesion analyzer 330 may output the indices of biomarker expression using a predetermined algorithm, a machine learning model (e.g., RNN, CNN, FCNN, and the like among artificial neural network models). In an embodiment, the lesion analyzer 330 may correspond to the first machine learning model. According to an embodiment, the lesion analyzer 330 may predict the indices of biomarker expression for the at least one lesion included in the medical image based on the medical image, the partial images, and/or the concatenated images and output the result.

In terms of learning, the lesion analyzer 330 may be trained to make a prediction related to expression of a specific biomarker in a lesion with a variety of data and methods. For example, the lesion analyzer 330 may be trained with actual expression levels of a biomarker identified in a specific image (2D image, 3D image, and the like). In this case, the actual expression levels of the biomarker may refer to expression levels identified by a clinical method such as tissue collection and the like. According to an embodiment, since the number of 3D medical images may be limited compared to 2D medical images, data collection may be difficult. In this case, the processor 220 may input 2D axial image to 2D CNN model to train the model, and dilate the parameters of the trained model into 3D parameters. With such a configuration, the processor 220 may fine-tune the 3D image data to generate a 3D image model utilizing the knowledge obtained through 2D image learning.

According to an embodiment, the lesion analyzer 330 may predict the indices of biomarker expression for the at least one lesion included in the medical image by using the medical image and at least one piece of additional information and output the result. For example, the lesion analyzer 330 may determine segmentation information of the at least one lesion included in the medical image, and predict the indices of biomarker expression by using the corresponding segmentation information. In another example, the lesion analyzer 330 may acquire patient information associated with the medical image and predict the indices of biomarker expression by using the corresponding patient information. In still another example, the lesion analyzer 330 may acquire lesion information representing at least one lesion, and predict the indices of biomarker expression using the corresponding lesion information. In this case, the lesion analyzer 330 may use the segmentation information, the patient information, the lesion information, and the like encoded in vector form as the additional information for predicting the indices of biomarker expression.

Additionally or alternatively, the lesion analyzer 330 may receive another medical image (e.g., second medical image) captured at a point in time different from the medical image (e.g., first medical image), and use another medical image to predict the indices of biomarker expression. For example, the lesion analyzer 330 may extract regions for the lesion from the medical image and another medical image, and classify the same lesion from each image. Then, the lesion analyzer 330 may predict the indices of biomarker expression based on changes in the lesions classified as the same lesion.

Additionally or alternatively, the lesion analyzer 330 may predict an index of biomarker expression for another lesion included in the medical image based on the actual indices of biomarker expression extracted for one lesion included in the medical image and output the result. In other words, the lesion analyzer 330 may acquire an index of biomarker expression for the lesion different from at least one lesion in the medical image, and use the acquired index of biomarker expression for the different lesion and the generated partial images to output the indices of biomarker expression for the at least one lesion included in the medical image.

According to an embodiment, the processor 220 may extract regions for a plurality of lesions from the received medical image and crop the extracted regions for the plurality of lesions to generate a plurality of partial images. In this case, the processor 220 may input the plurality of generated partial images to the second machine learning model to output features of each of the plurality of partial images. In this example, the second machine learning model may include a feature extraction model implemented as any machine learning model (e.g., RNN, CNN, FCNN, and the like among artificial neural network models). A feature of each of the plurality of partial images output as described above may be used to predict or output an index of biomarker expression for each of the plurality of lesions. Additionally or alternatively, the second machine learning model may be configured to receive not only the partial images, but also the whole medical image. In this case, the overall state of the patient included in the medical image may be considered when predicting an index of expression of a specific biomarker in the lesion of the patient, by encoding the overall state of the patient with respect to the medical image.

The tissue collection analyzer 340 may output information associated with the tissue collection of the at least one lesion using the output indices of biomarker expression. The tissue collection analyzer 340 may output information associated with the tissue collection using a predetermined algorithm, a machine learning model (e.g., RNN, CNN, FCNN, and the like among artificial neural network models), and the like, and for example, the tissue collection analyzer 340 may correspond to a third machine learning model. In addition, the information associated with the tissue collection may include a location and a size of tissue collection for the lesion, a priority of tissue collection, a method of tissue collection, and the like. For example, the tissue collection method may include a percutaneous needle biopsy in which cells are acquired by piercing a needle into an affected area, and an open biopsy in which tissue is directly collected by incising the affected area, and the like, in which case the tissue collection analyzer 340 may output information indicating the suitability of a specific biopsy according to the location and size of the lesion, and the like.

The at least one lesion included in the medical image may include a plurality of lesions included in the medical image, in which case the tissue collection analyzer 340 may output information on a priority of tissue collection for the plurality of lesions. For example, the information on the priority of tissue collection may include a priority for each of lesions among a plurality of lesions suitable for tissue collection, which is determined based on the indices of biomarker expression, and the like. According to an embodiment, the tissue collection analyzer 340 may acquire reference information on tissue collection associated with the medical image, and use the output indices of biomarker expression and the acquired reference information on tissue collection to output the information on a priority of tissue collection for a plurality of lesions. In this case, the reference information on tissue collection is any information that can be used together with the indices of biomarker expression, and the like to determine the suitability of tissue collection, and may include information on the patient's underlying medical condition history, risk of surgery (e.g., whether or not large blood vessels and major organs are located in the vicinity of the lesion), location of lesions (e.g., whether or not the lesion is in a location where percutaneous access is possible), size of lesions (e.g., whether or not the lesion is in such a size that allows sample extraction (e.g., 1 cm or more)), and the like.

Although the components of the processor 220 have been described separately for each function in FIG. 3, it does not necessarily mean that they are physically separated. For example, the lesion detector 320 and the lesion analyzer 330 have been described above as separate components, but this is for better understanding of the disclosure, and embodiments are not limited thereto. For example, the lesion detector 320, the lesion analyzer 330, and the tissue collection analyzer 340 may be implemented through one artificial neural network model, or may be implemented through a plurality of different artificial neural network models. With such a configuration, the processor 220 may predict regions, indices of biomarker expression, etc. for each lesion, and use the predicted indices of biomarker expression for the region for each lesion, the reference information on tissue collection, etc. to simply determine the most suitable lesion to perform tissue collection. In addition, when provided with the information on the lesion determined as described above, the doctor can directly perform tissue collection on a patient without having to go through unnecessary tissue collection processes, thus eliminating the discomfort that the patient may feel, and also without significantly affecting the patient's probability of survival.

Figure 4:
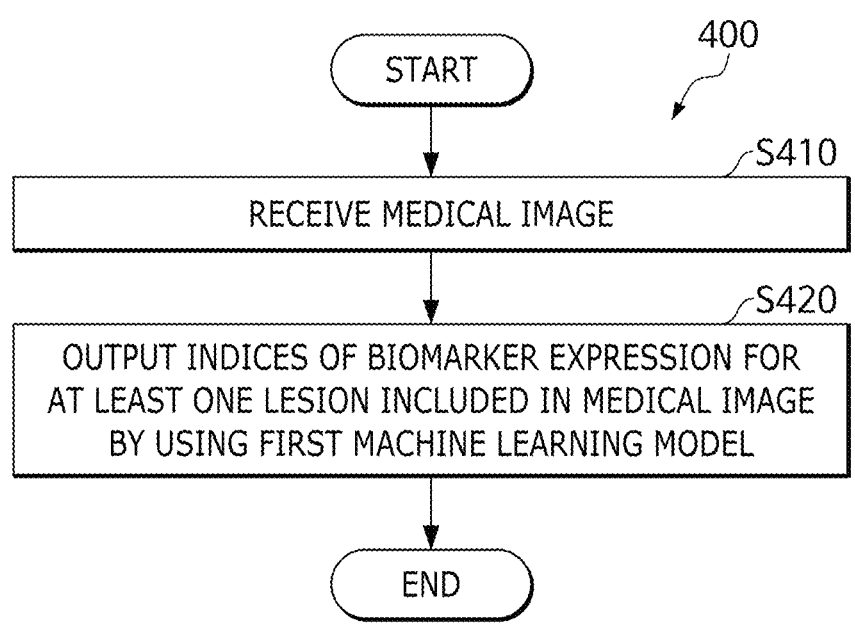
FIG. 4 is a flowchart illustrating a method for predicting biomarker expression from a medical image according to an embodiment.

FIG. 4 is a flowchart illustrating a method 400 for predicting biomarker expression from a medical image according to an embodiment. According to an embodiment, the method 400 for predicting biomarker expression may be performed by a processor (e.g., a processor of a user terminal and/or at least one processor of an information processing system). As illustrated, the method 400 for predicting biomarker expression may be started by the processor receiving a medical image, at S410. For example, the processor may directly capture the medical image using any device associated with the information processing system, or receive the medical image from an external device (e.g., a user terminal or a database).

The processor may output indices of biomarker expression for the at least one lesion included in the medical image by using the first machine learning model, at S420. According to an embodiment, the processor may extract the regions for the at least one lesion from the received medical image. In this case, the region for the lesion may include at least one of a location and a size of the lesion. Then, the processor may crop the extracted regions for the at least one lesion from the medical image to generate partial images. In addition, the processor may input the generated partial images to the first machine learning model to output the indices of biomarker expression for the at least one lesion.

According to an embodiment, the processor may input the received medical image and the generated partial images to the first machine learning model to output the indices of biomarker expression for the at least one lesion. Additionally or alternatively, the processor may adjust the size of the received medical image and the sizes of the generated partial images to a predetermined size, and concatenate the adjusted medical image and the adjusted partial images to generate concatenated images. Then, the processor may input the concatenated images to the first machine learning model to output the indices of biomarker expression for the at least one lesion.

Figure 5:
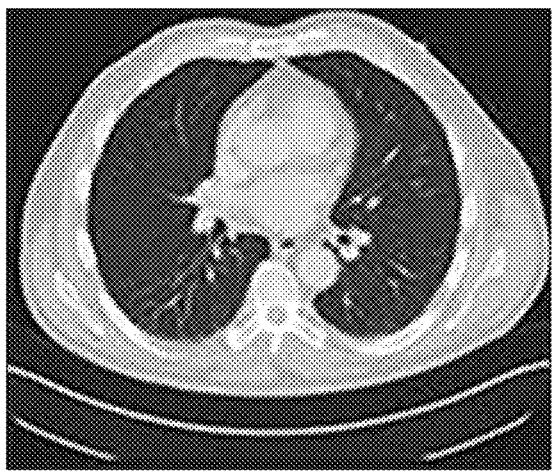
FIG. 5 is a diagram illustrating an example of generating a medical image that shows regions for lesions according to an embodiment.
Figure 5:
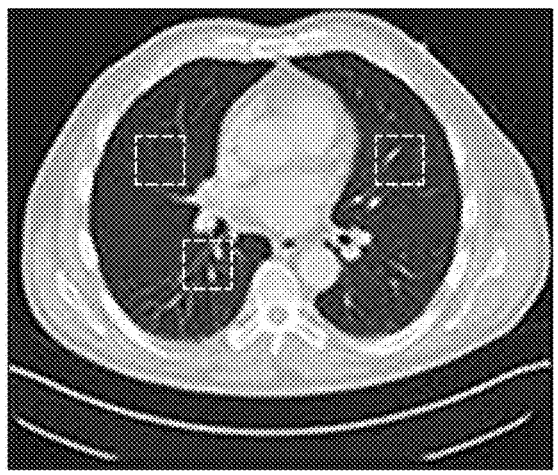

FIG. 5 is a diagram illustrating an example of generating a medical image 520 that shows regions for lesions according to an embodiment. As described above, the processor (e.g., at least one processor of the information processing system, and the like) may receive a medical image 510 associated with a specific patient. In the illustrated example, the medical image 510 is illustrated as being a CT image associated with a patient, but is not limited thereto, and it may include any image and the like associated with the patient, such as a 2D image, a 3D image, or a synthetic image, and the like of MRI, PET, SPECT, DBT, and the like, for example.

According to an embodiment, the processor may extract regions for the lesion from the medical image 510 and generate the medical image 520 that shows the regions for the lesion. For example, the processor may input the medical image 510 to the lesion detector to detect the regions for the lesion, and generate the medical image 520 that shows the detected regions for the lesion. In this case, the region for the lesion may include a location, a size, and the like of the lesion.

FIG. 5 illustrates the medical image 520 with the regions for the lesions displayed in the form of rectangular boxes, but embodiments are not limited thereto, and the regions for the lesions may be displayed in the form of any polygon, form of an outline of the lesion, and the like. In addition, FIG. 5 illustrates that the regions for the lesions are displayed in the medical image 520, but embodiments are not limited thereto, and the processor may extract the regions for the at least one lesion from the received medical image 510, and crop the extracted regions for the at least one lesion from the medical image 510 to generate and output the partial images on the display device. In addition, although not illustrated in FIG. 5, the medical image 520 may display not only the regions for the lesion, but also information on the lesion and the like.

Figure 6:
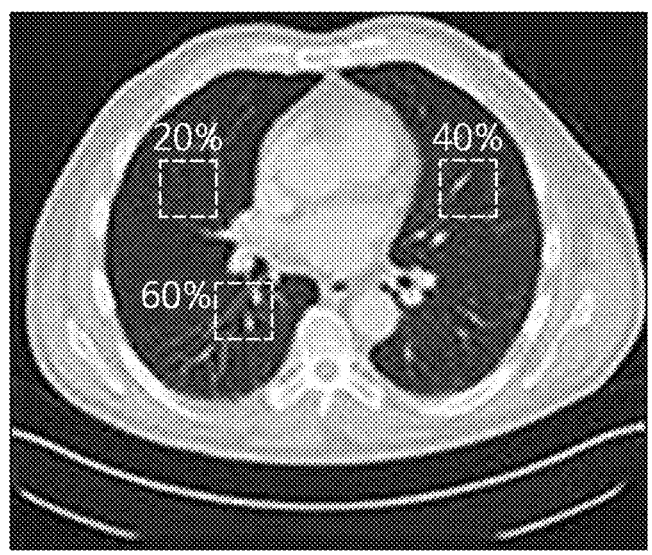
FIG. 6 is a diagram illustrating an example of generating an image that shows indices of biomarker expression according to an embodiment.

FIG. 6 is a diagram illustrating an example of generating an image that shows indices of biomarker expression according to an embodiment. As illustrated in FIG. 6, the indices of biomarker expression may be output for each of the regions for the lesion detected from the medical image. According to an embodiment, the processor may output the indices of biomarker expression for the at least one lesion included in the medical image by using the first machine learning model. For example, the first machine learning model may be configured to output indices of expression of a specific biomarker for the at least one lesion included in the medical image. In this example, the specific biomarker may be one or more biomarkers. Then, an image 610 showing the output indices of biomarker expression may be output or displayed.

As described above, the biomarker may refer to the index that can indicate changes in the body using proteins, DNA, RNA, metabolites, and the like. That is, the biomarkers may be different for each disease, and there may be a plurality of biomarkers different from each other even for the same disease. In this case, the biomarker extracted from the medical image may be selected by the user, or determined or specified based on the regions for the detected lesion. In other words, the processor may predict the indices of expression of a specific biomarker and output the result.

FIG. 6 illustrates that the index of biomarker expression for each lesion is output in percentage (%), but embodiments are not limited thereto, and it may be output in the form of scores. In addition, FIG. 6 illustrates that only the indices of biomarker expression are displayed, but embodiments are not limited thereto, and information associated with the corresponding biomarker (e.g., name of the disease associated with the corresponding biomarker, name of the corresponding biomarker, and the like) may also be output together with the indices of biomarker expression. With such a configuration, the user can check the output indices of biomarker expression and then start collecting tissues from a lesion with a highest probability of biomarker expression, thereby minimizing the burden on the patient for tissue collection.

Figure 7:
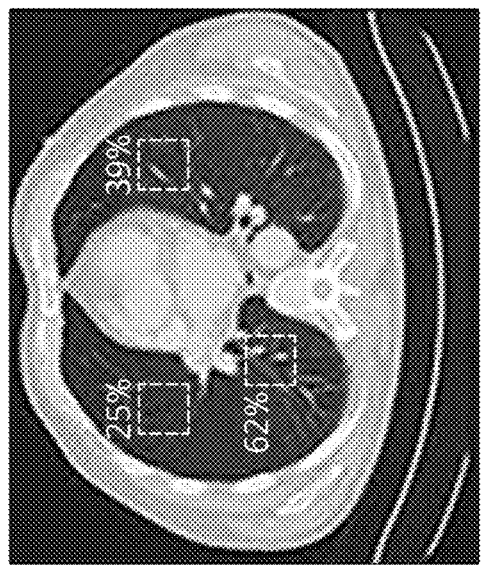
FIG. 7 is a diagram illustrating an example of receiving a second medical image captured at a point in time different from the first medical image and outputting indices of biomarker expression for the first medical image according to an embodiment.
Figure 7:
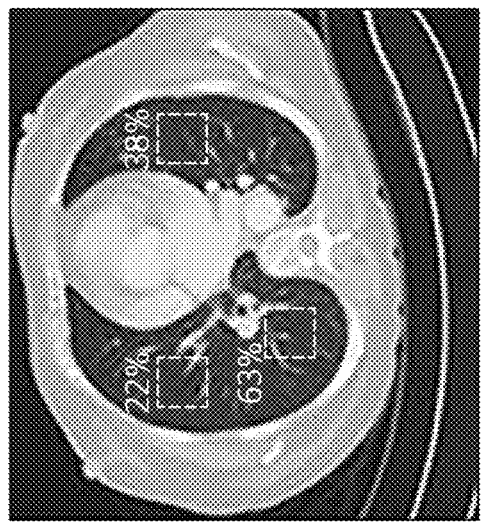
Figure 7:
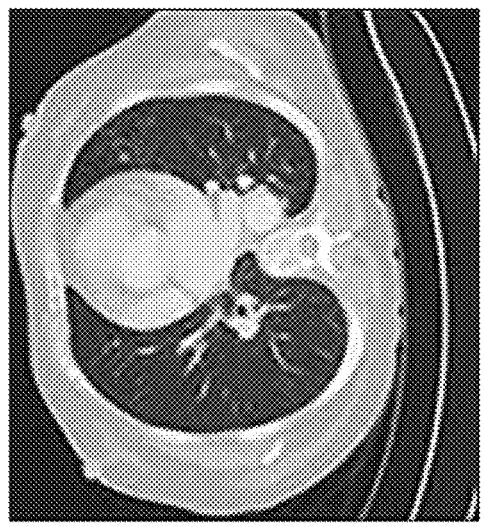

FIG. 7 is a diagram illustrating an example of receiving a second medical image 710 captured at a point in time different from the first medical image and outputting indices of biomarker expression for the first medical image according to an embodiment. As described above, the processor may receive the medical image and output indices of biomarker expression. In this case, the processor may receive the first medical image (e.g., 510 in FIG. 5) and the second medical image 710 captured at a point in time different from the first medical image, and output the indices of biomarker expression. In this case, the first medical image and the second medical image may correspond to images acquired by capturing the same or similar body parts of the same patient.

According to an embodiment, the processor may extract the regions for the at least one lesion from each of the first medical image and the second medical image 710. Then, the regions for the at least one lesion extracted from the first medical image and the regions for the at least one lesion extracted from the second medical image 710 may be input to the first machine learning model and the indices of biomarker expression for the at least one lesion may be output.

To this end, the processor may extract the regions for the lesion from the second medical image 710, predict the indices of biomarker expression for the extracted regions for the lesion, and output an image 720 that shows the predicted indices of biomarker expression on the display device or the like. In another example, the processor may receive previously predicted indices of biomarker expression for each lesion with respect to the second medical image 710 from an external system or the like.

Then, the processor may predict the indices of biomarker expression in the first medical image by using information on the indices of biomarker expression predicted from not only the first medical image, but also the second medical image 710. The processor may output or display an image 730 that shows the indices of biomarker expression in the first medical image predicted as described above on the display device or the like. As such, the indices of biomarker expression predicted using both the first medical image and the second medical image 710 may be different from the indices of biomarker expression predicted using the first medical image only.

FIG. 7 illustrates that the index of biomarker expression for each lesion is output in percentage (%), but embodiments are not limited thereto, and it may be output in the form of scores. In addition, FIG. 7 illustrates that only the indices of biomarker expression is displayed, but embodiments are not limited thereto, and information associated with the corresponding biomarker (e.g., name of the disease, name of the corresponding biomarker, and the like) may also be output together with the indices of biomarker expression. With such a configuration, the processor may use not only the first medical image but also the second medical image captured at a point in time different from the first medical image to predict the indices of biomarker expression in the first medical image, thereby more accurately predicting the indices of expression of the specific biomarker of the lesion.

Figure 8:
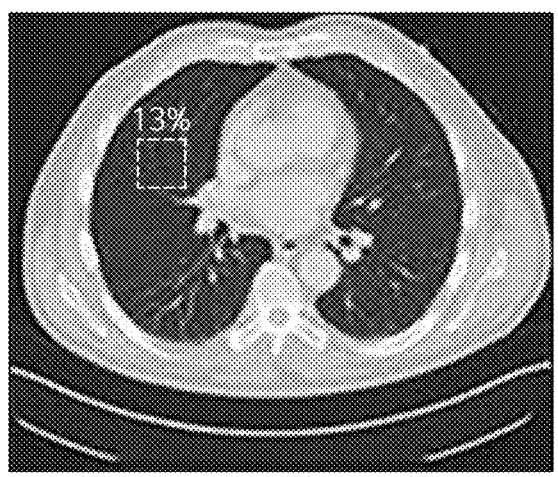
FIG. 8 is a diagram illustrating an example of predicting indices of biomarker expression for a specific lesion by using an index of biomarker expression for a different lesion according to an embodiment.
Figure 8:
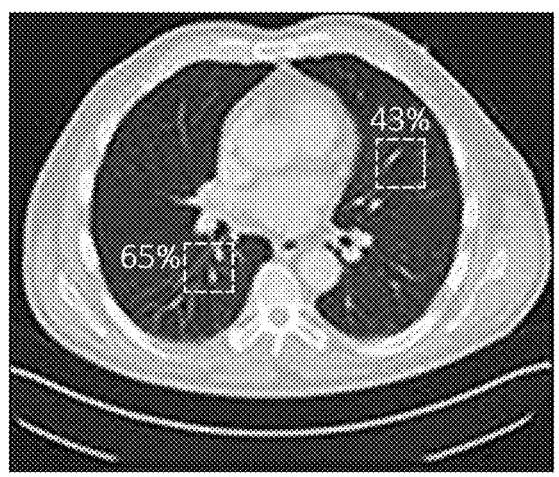

FIG. 8 is a diagram illustrating an example of predicting indices of biomarker expression for a specific lesion by using an index of biomarker expression for a different lesion according to an embodiment. According to an embodiment, the processor may acquire an index of biomarker expression for a lesion different from the at least one lesion in the medical image. In this example, the biomarker of the different lesion may be the same as or different from the biomarker of the at least one lesion in the medical image. For example, when the biomarker of the at least one lesion in the medical image is PD-L1, the biomarker of the different lesion may correspond to PD-L1, EGFR, DCIS, ALK, and the like.

According to an embodiment, an image 810 that shows the index of biomarker expression of the different lesion may be output to the display device or the like. In this case, the processor may input the acquired index of biomarker expression of the different lesion and partial images generated by cropping the regions for the lesion included in the medical image into the first machine learning model to output the indices of biomarker expression for the at least one lesion included in the medical image. In this case, the first machine learning model may be trained to output the indices of biomarker expression for the at least one lesion based on the partial images including the regions for the at least one lesion, and the information on the index of expression for the different lesion. In addition, the index of biomarker expression of the different lesion may include not only a predicted index of biomarker expression of the different lesion output through the machine learning model, but also the actual amount of biomarker expression of the different lesion identified by the actual tissue collection or the like.

According to this method, the processor can predict the indices of biomarker expression for the at least one lesion in the medical image by using not only the received medical image, but also the information on the index of biomarker expression of the different lesion. Then, the processor may display, on the display device or the like, an image 820 that shows the predicted indices of biomarker expression for the at least one lesion in the medical image. As such, the indices of biomarker expression of the at least one lesion in the medical image, which are predicted using both the medical image and the index of biomarker expression of the different lesion, may be different from the indices of biomarker expression predicted using the medical image only.

FIG. 8 illustrates that only the indices of biomarker expression is displayed, but embodiments are not limited thereto, and information associated with the corresponding biomarker (e.g., name of the disease, name of the corresponding biomarker, and the like) may also be output together with the indices of biomarker expression. With such a configuration, the processor can predict the indices of biomarker expression for the at least one lesion included in the medical image by using the index of biomarker expression for the lesion different from the at least one lesion, thereby outputting a more accurate prediction result.

Figure 9:
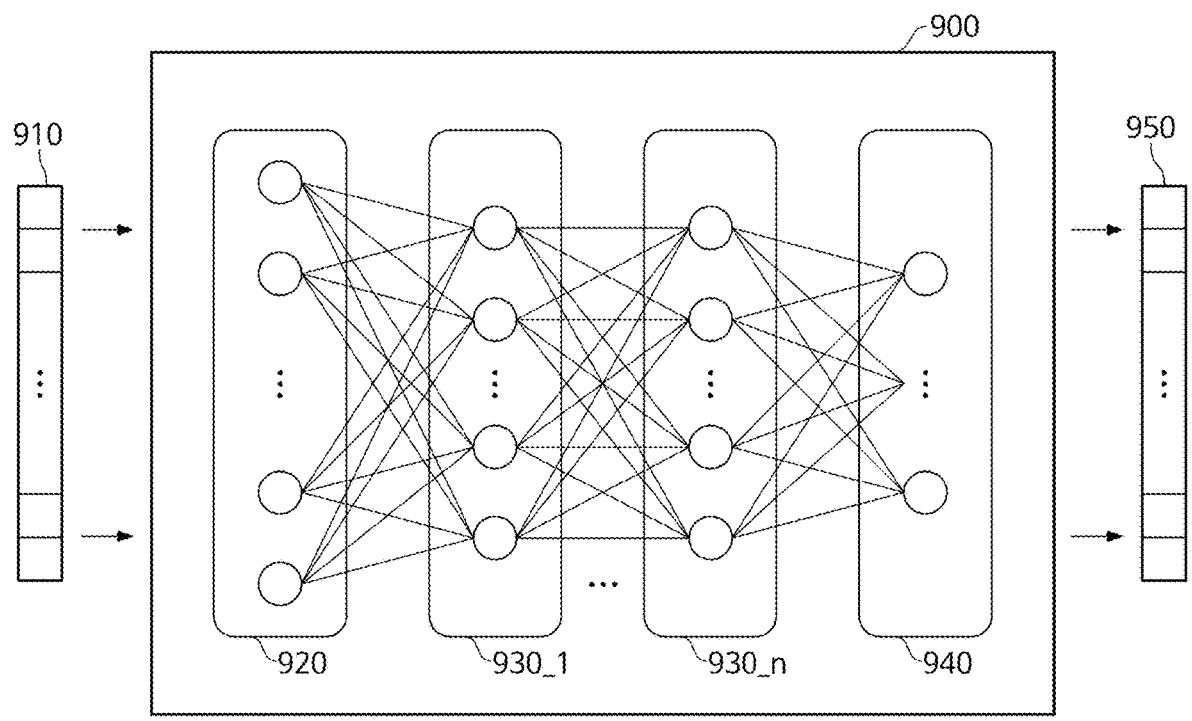
FIG. 9 is an exemplary diagram illustrating an artificial neural network model according to an exemplary embodiment.

FIG. 9 is an exemplary diagram illustrating an artificial neural network model 900 according to an embodiment. In machine learning technology and cognitive science, an artificial neural network model 900 as an example of the machine learning model refers to a statistical learning algorithm implemented based on a structure of a biological neural network, or to a structure that executes such algorithm.

According to an embodiment, the artificial neural network model 900 may represent a machine learning model that acquires a problem solving ability by repeatedly adjusting the weights of synapses by the nodes that are artificial neurons forming the network through synaptic combinations as in the biological neural networks, thus training to reduce errors between a target output corresponding to a specific input and a deduced output. For example, the artificial neural network model 900 may include any probability model, neural network model, and the like, that is used in artificial intelligence learning methods such as machine learning and deep learning.

According to an embodiment, the lesion detector, the lesion analyzer, and/or the tissue collection analyzer described above may be generated in the form of the artificial neural network model 900 as a form of a machine learning model. For example, the artificial neural network model 900 may receive a medical image and output indices of biomarker expression for the at least one lesion included in the medical image. In another example, the processor may extract regions for the at least one lesion from the received medical image using the artificial neural network model 900, and crop the extracted regions for the at least one lesion from the medical image to generate partial images. In still another example, the artificial neural network model 900 may be configured to use a plurality of partial images to output features of each of the plurality of partial images. In still another example, the artificial neural network model 900 may be configured to output information associated with tissue collection for the at least one lesion by using the output indices of biomarker expression.

The artificial neural network model 900 is implemented as a multilayer perceptron (MLP) formed of multiple nodes and connections between them. The artificial neural network model 900 according to an embodiment may be implemented using one of various artificial neural network model structures including the MLP. As shown in FIG. 9, the artificial neural network model 900 includes an input layer 920 to receive an input signal or data 910 from the outside, an output layer 940 to output an output signal or data 950 corresponding to the input data, and (n) number of hidden layers 930_1 to 930_n (where n is a positive integer) positioned between the input layer 920 and the output layer 940 to receive a signal from the input layer 920, extract the features, and transmit the features to the output layer 940. In an example, the output layer 940 receives signals from the hidden layers 930_1 to 930_n and outputs them to the outside.

The method of training the artificial neural network model 900 includes the supervised learning that trains to optimize for solving a problem with inputs of teacher signals (correct answers), and the unsupervised learning that does not require a teacher signal. The information processing system may train, by the supervised and/or unsupervised learning, the artificial neural network model 900 that is trained to infer the indices of biomarker expression for the at least one lesion included in the medical image. The artificial neural network model 900 trained as described above may be stored in a memory (not illustrated) of the information processing system, and output the indices of biomarker expression for the at least one lesion included in the medical image received from the communication module and/or memory.

According to an embodiment, the input variable of the artificial neural network model 900 may be the medical image, the partial images, and/or the concatenated images. Additionally or alternatively, the input variable of the artificial neural network model 900 may include additional information such as segmentation information, patient information, lesion information, and the like. That is, a vector indicating or characterizing the image, the additional information, and the like described above may be input through the input layer 920. As described above, when the input variable described above is input through the input layer 920, the output variable output from the output layer 940 of the artificial neural network model 900 may be the vector indicating or characterizing the indices of biomarker expression for the at least one lesion included in the image.

As described above, the input layer 920 and the output layer 940 of the artificial neural network model 900 are respectively matched with a plurality of output variables corresponding to a plurality of input variables, and the synaptic values between nodes included in the input layer 920, the hidden layers 930_1 to 930_n, and the output layer 940 are adjusted, so that by training, a correct output corresponding to a specific input can be extracted. Through this training process, the features hidden in the input variables of the artificial neural network model 900 may be confirmed, and the synaptic values (or weights) between the nodes of the artificial neural network model 900 may be adjusted so as to reduce the errors between the output variable calculated based on the input variable and the target output. By using the artificial neural network model 900 trained as described above, the indices of biomarker expression for the at least one lesion included in the received medical image may be output.

Figure 10:
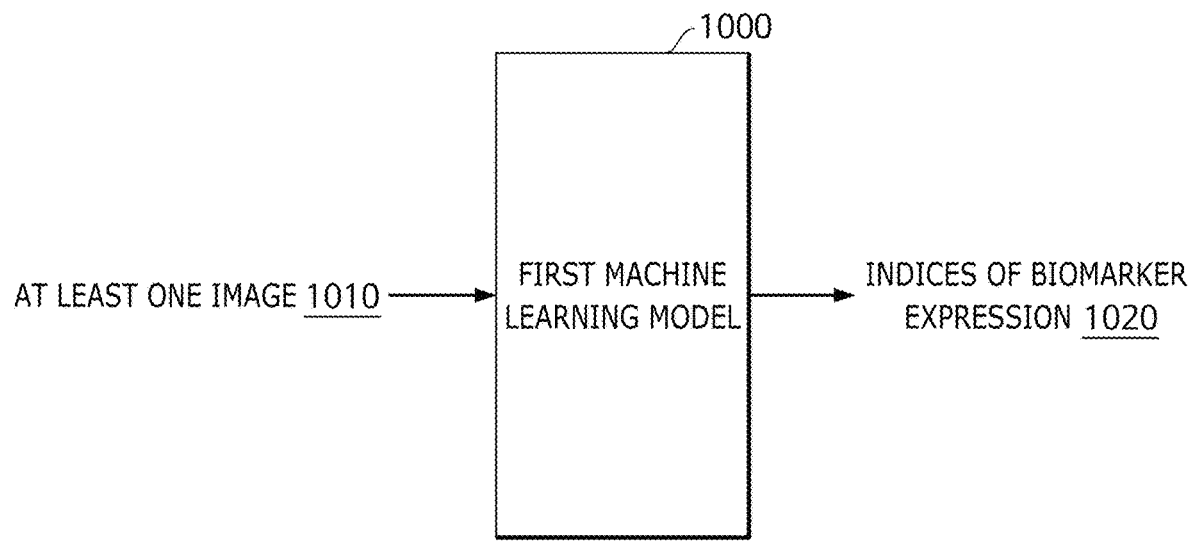
FIG. 10 is a diagram illustrating an example in which a first machine learning model outputs indices of biomarker expression by using at least one image according to an embodiment.

FIG. 10 is a diagram illustrating an example in which a first machine learning model 1000 outputs indices 1020 of biomarker expression by using at least one image 1010 according to an embodiment. As illustrated, the first machine learning model 1000 may output the indices 1020 of biomarker expression for the at least one lesion included in the at least one image 1010. In this case, the at least one image 1010 may include the medical image, and the concatenated images that are generated by concatenating, in the medical image, the partial images generated by cropping the regions for the at least one lesion from the medical images and/or the medical image and partial images adjusted in size.

According to an embodiment, the first machine learning model 1000 may receive the medical image and output the indices 1020 of biomarker expression for the at least one lesion included in the medical image. For example, the first machine learning model 1000 may extract the regions for the at least one lesion from the received medical image, predict the indices of biomarker expression for each of the extracted regions for the at least one lesion and output the result. In another example, the first machine learning model 1000 may receive the medical image from which the regions for the at least one lesion are extracted, predict the indices of biomarker expression for each of the regions for the at least one lesion from the corresponding medical image and output the result.

According to another embodiment, the first machine learning model 1000 may output the indices 1020 of biomarker expression for the at least one lesion by using the partial images generated by cropping the extracted regions for the at least one lesion from the medical image. In this case, the first machine learning model 1000 may output the indices 1020 of biomarker expression for the at least one lesion by using the medical image and the generated partial images. With such a configuration, the first machine learning model 1000 may use the partial images including only the extracted regions of the lesion to remove noise and/or errors due to regions other than the lesion included in the medical image, thereby more accurately predicting the indices 1020 of biomarker expression.

According to still another embodiment, the first machine learning model 1000 may output the indices 1020 of biomarker expression for the at least one lesion by using the concatenated images generated by concatenating the medical image and partial images adjusted in size. According to an embodiment, the processor may adjust the size of the received medical image and the size of the generated partial images to a predetermined size, and concatenate the adjusted medical image and the adjusted partial images to generate the concatenated images. In other words, the processor may receive the concatenated images as described above as an input of the first machine learning model 1000 and output the indices 1020 of biomarker expression through the first machine learning model 1000.

Figure 11:
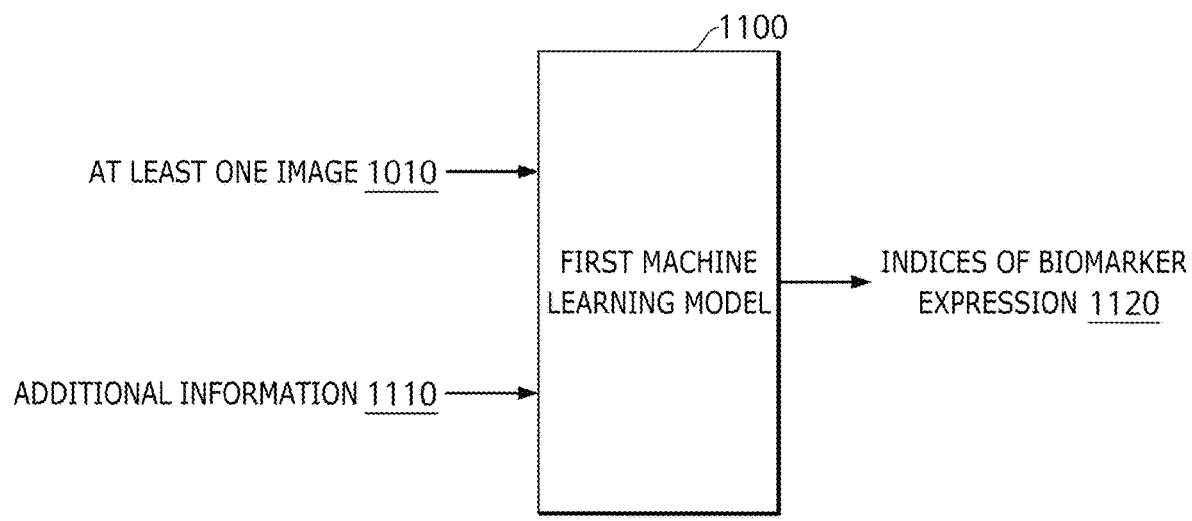
FIG. 11 is a diagram illustrating an example in which the first machine learning model outputs indices of biomarker expression by using at least one image and additional information according to an embodiment.

FIG. 11 is a diagram illustrating an example in which the first machine learning model 1100 outputs indices 1120 of biomarker expression by using the at least one image 1010 and the additional information 1110 according to an embodiment. As described above, the processor may output the indices 1120 of biomarker expression for the at least one lesion included in the at least one image 1010 through the first machine learning model 1100. In this case, the first machine learning model 1100 may be configured to output the indices 1120 of biomarker expression by using the additional information 1110 together with the at least one image 1010. In this case, the additional information 1110 may include segmentation information, patient information, and/or lesion information, and the like.

According to an embodiment, the processor may input the segmentation information and the at least one image 1010 of the at least one lesion to the first machine learning model 1100 to output the indices 1120 of biomarker expression for the at least one lesion included in the medical image. In this example, the segmentation information may refer to any information associated with the shape of the lesion, such as soft tissue, calcification, cavity, ground glass opacity, and the like. That is, the processor may predict or determine the segmentation information of the at least one lesion included in the corresponding medical image based on the medical image. For example, the processor may predict the segmentation of the at least one lesion by using a machine learning model trained to predict the segmentation of the at least one lesion in the medical image. The segmentation information determined as described above may be used to predict the indices 1120 of biomarker expression.

Additionally or alternatively, the processor may acquire patient information associated with the medical image, and input the acquired patient information and the at least one image 1010 to the first machine learning model 1100 to output the indices 1120 of biomarker expression for the at least one lesion included in the medical image. In this case, the patient information may include basic information, diagnostic information, history information, and the like of the patient associated with the image, and may include, for example, information on at least one of the patient's age, gender, smoking history, previous medical history, treatment history, or family medical history. In other words, the patient information acquired as described above may be used to predict the indices 1120 of biomarker expression.

Additionally or alternatively, the processor may acquire lesion information associated with the medical image, and input the acquired lesion information and the at least one image 1010 to the first machine learning model 1100 to output the indices 1120 of biomarker expression for the at least one lesion included in the medical image. In this case, the lesion information may be any information associated with the lesion, and may include information associated with the size, the location, and the shape and the like of the lesion, such as the size of the lesion, the location of the lesion, spiculated, lobulated, calcified, cavity, solid, non-solid, par-solid, and the like, for example. In other words, the lesion information acquired as described above may be used to predict the indices 1120 of biomarker expression. With such a configuration, the processor may further input not only the at least one image 1010, but also the at least one additional information 1110 to the first machine learning model 1100 to more accurately predict the indices 1120 of biomarker expression and output the result.

Figure 12:
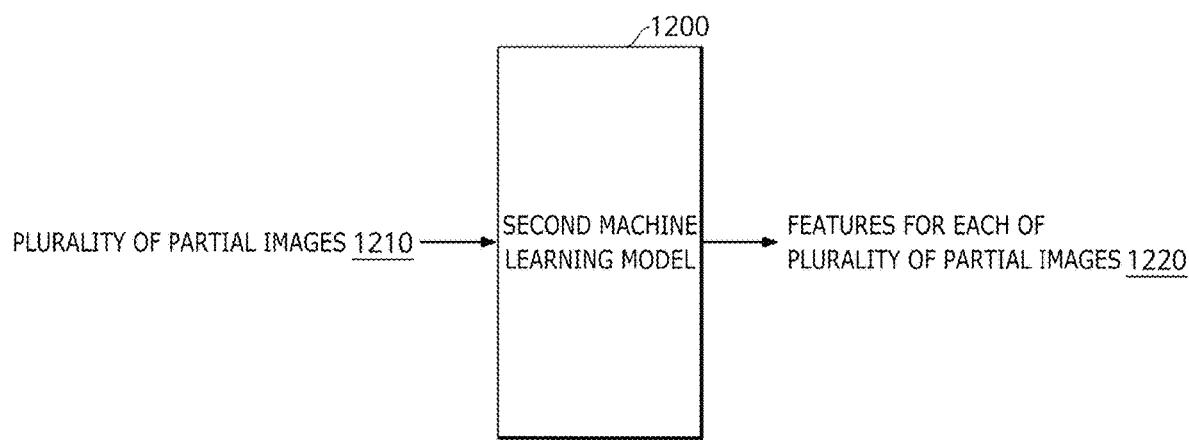
FIG. 12 is a diagram illustrating an example in which a second machine learning model outputs a feature of each of a plurality of partial images by using a plurality of partial images according to an embodiment.

FIG. 12 is a diagram illustrating an example in which a second machine learning model 1200 outputs a feature 1220 of each of a plurality of partial images by using a plurality of partial images 1210 according to an embodiment. As described above, the second machine learning model 1200 may refer to a feature extraction model. That is, the second machine learning model 1200 may extract a feature of each lesion included in the plurality of partial images 1210. In this case, the feature of the lesion may refer to any information that can indicate or characterize each lesion, and may include location and size of the lesion, shape of the lesion, nature of the lesion, type of lesion, and the like, for example, but is not limited thereto.

According to an embodiment, the at least one lesion included in the medical image may include a plurality of lesions included in the medical image. In this case, the processor may extract regions for a plurality of lesions from the received medical image and crop the extracted regions for the plurality of lesions to generate the plurality of partial images 1210. The plurality of partial images 1210 generated as described above may be used as input data of the second machine learning model 1200.

According to an embodiment, the second machine learning model 1200 may output the feature 1220 of each of the plurality of partial images by using the generated plurality of partial images. In this case, the second machine learning model 1200 may be configured to output the feature 1220 of each of the plurality of partial images. As described above, the feature 1220 of each of the output plurality of partial images may be used as the input data 1010 of the first machine learning model (1000 in FIG. 10) to output the indices of biomarker expression for each of the plurality of lesions or used as the additional information 1110 of the first machine learning model (1100 in FIG. 11). With such a configuration, the first machine learning model can further utilize the feature 1220 of not only the medical images, but also each of the plurality of partial images, thereby more accurately predicting and outputting the indices of biomarker expression.

FIG. 12 illustrates that the second machine learning model 1200 inputs the plurality of partial images 1210 of a patient to output the feature 1220 of each of the plurality of partial images, but embodiments are not limited thereto, and the processor may be configured to input the whole medical image including the plurality of partial images 1210 to the second machine learning model 1200 to output the feature 1220 of each of the plurality of partial images. In this case, since the whole medical image is received, the overall state of the corresponding patient may be encoded, and the encoded information may be used to output the feature 1220 of the plurality of partial images 1210.

Figure 13:
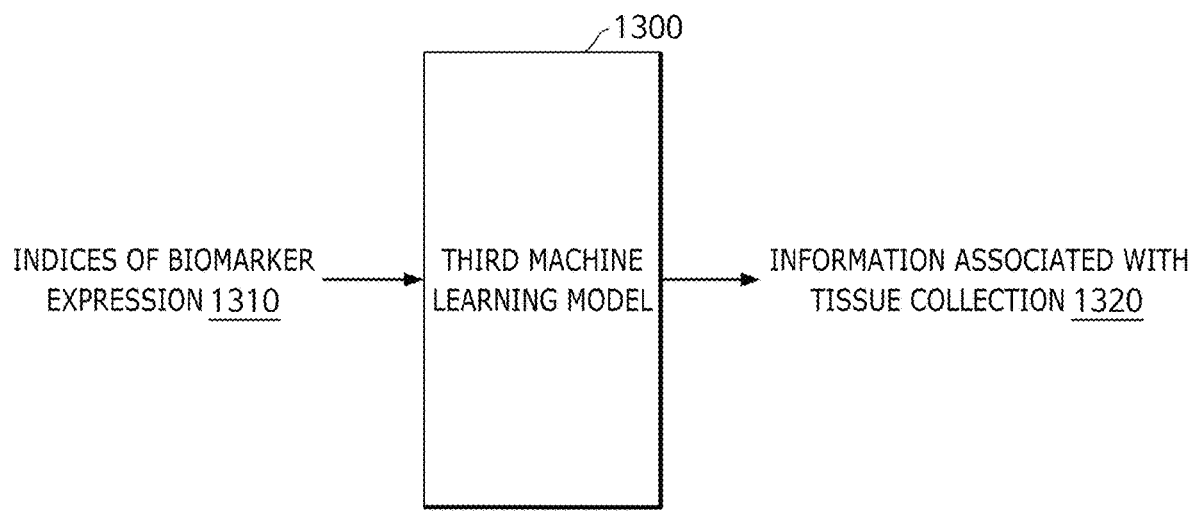
FIG. 13 is a diagram illustrating an example in which a third machine learning model outputs information associated with tissue collection by using indices of biomarker expression according to an embodiment.

FIG. 13 is a diagram illustrating an example in which a third machine learning model 1300 outputs information 1320 associated with tissue collection by using indices 1310 of biomarker expression according to an embodiment. As illustrated, the third machine learning model 1300 may receive the indices 1310 of biomarker expression and output the information 1320 associated with tissue collection. That is, the processor may not only extract the indices 1310 of biomarker expression, but also predict and output the information 1320 associated with tissue collection using the extracted indices 1310 of biomarker expression.

According to an embodiment, the indices 1310 of biomarker expression may be indices of biomarker expression for the at least one lesion included in the medical image, which may be output by the first machine learning model using the at least one image, the additional information, and the like, as described above. Additionally or alternatively, the indices 1310 of biomarker expression may be input by the user or received from any external system.

According to an embodiment, the third machine learning model 1300 may output the information 1320 associated with tissue collection and provide it to the user. The information 1320 associated with tissue collection may be any information that is necessary for the user to perform tissue collection for the lesion included in the medical image, and may include information on a method of tissue collection, a location of tissue collection, and a priority of tissue collection, although embodiments are not limited thereto. With such a configuration, the user can efficiently determine a lesion to collect the tissues, among the patient's lesions by using the information 1320 associated with tissue collection.

Figure 14:
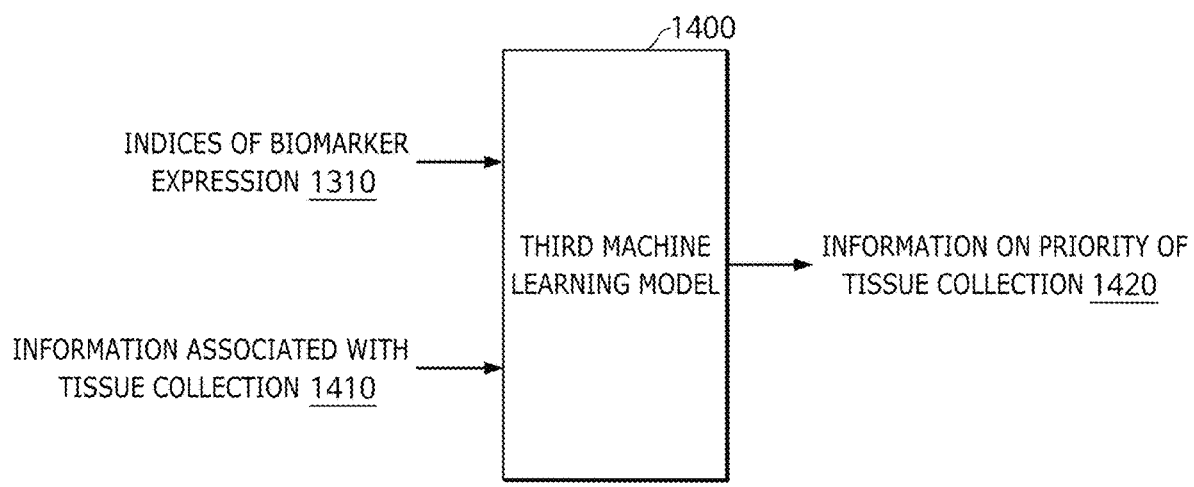
FIG. 14 is a diagram illustrating an example in which a third machine learning model outputs information on a priority of tissue collection by using the indices of biomarker expression and the reference information on tissue collection according to an embodiment.

FIG. 14 is a diagram illustrating an example in which a third machine learning model 1400 outputs output information 1420 on a priority of tissue collection by using the indices 1310 of biomarker expression and the reference information 1410 on tissue collection according to an embodiment. As illustrated, the third machine learning model 1400 may receive the indices 1310 of biomarker expression and the reference information 1410 on tissue collection, and output the information 1420 on a priority of tissue collection. In this case, the reference information 1410 on tissue collection may include information on the patient's underlying medical condition history, risk of surgery, ease of lesion access, ease of percutaneous lesion access, degree of expected damage during tissue collection, and/or the size of the lesion, and the like. For example, the reference information 1410 on tissue collection may include whether or not large blood vessels and major organs are located around the lesion, whether or not the lesion is in such a size that allows sample extraction, whether or not the size of the lesion is 1 cm or more, and the like.

According to an embodiment, the at least one lesion included in the medical image may include a plurality of lesions included in the medical image, in which case the third machine learning model 1400 may output the information 1420 on a priority of tissue collection for a plurality of lesions. In this case, the information 1420 on a priority of tissue collection may include information on an order, a priority, and the like of each lesion of the plurality of lesions to collect the tissue preferentially. With such a configuration, the user can easily determine which lesion of the lesions included in the medical image is to be preferentially examined in order to help the treatment of the patient.

Figure 15:
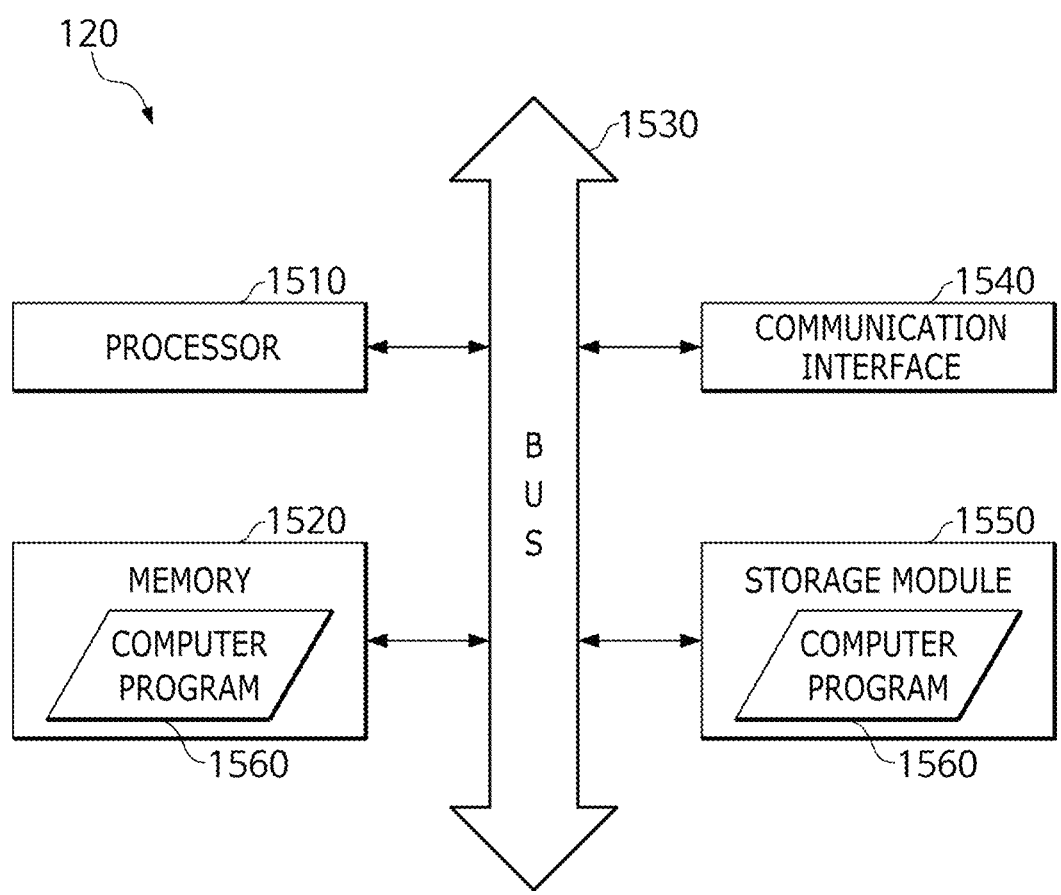
FIG. 15 is a configuration diagram of an exemplary system for performing an operation of predicting biomarker expression according to an embodiment.

FIG. 15 is a block diagram of any computing device 1500 associated with the operation of predicting biomarker expression according to an embodiment. For example, the computing device 1500 may include the information processing system 120 and/or the user terminal 130. As illustrated, the computing device 1500 may include one or more processors 1510, a bus 1530, a communication interface 1540, a memory 1520 for loading a computer program 1560 to be executed by the processors 1510, and a storage module 1550 for storing the computer program 1560. However, only the components related to the embodiment of the present disclosure are illustrated in FIG. 15. Accordingly, those of ordinary skill in the art to which the present disclosure pertains will be able to recognize that other general-purpose components may be further included in addition to the components shown in FIG. 15.

The processors 1510 control the overall operation of each component of the computing device 1500. The processors 1510 may be configured to include a central processing unit (CPU), a microprocessor unit (MPU), a micro controller unit (MCU), a graphic processing unit (GPU), or any type of processor well known in the technical field of the present disclosure. In addition, the processors 1510 may perform an arithmetic operation on at least one application or program for executing the method according to the embodiments of the present disclosure. The computing device 1500 may include one or more processors.

The memory 1520 may store various types of data, commands, and/or information. The memory 1520 may load one or more computer programs 1560 from the storage module 1550 in order to execute the method/operation according to various embodiments of the present disclosure. The memory 1520 may be implemented as a volatile memory such as RAM, but the technical scope of the present disclosure is not limited thereto.

The bus 1530 may provide a communication function between components of the computing device 1500. The bus 1530 may be implemented as various types of buses such as an address bus, a data bus, a control bus, or the like.

The communication interface 1540 may support wired/wireless Internet communication of the computing device 1500. In addition, the communication interface 1540 may support various other communication methods in addition to the Internet communication. To this end, the communication interface 1540 may be configured to include a communication module well known in the technical field of the present disclosure.

The storage module 1550 may non-temporarily store one or more computer programs 1560. The storage module 1550 may be configured to include a nonvolatile memory such as a read only memory (ROM), an erasable programmable ROM (EPROM), an electrically erasable programmable ROM (EEPROM), a flash memory, and the like, a hard disk, a detachable disk, or any type of computer-readable recording medium well known in the art to which the present disclosure pertains.

The computer program 1560 may include one or more instructions that, when loaded into the memory 1520, cause the processors 1510 to perform an operation/method in accordance with various embodiments of the present disclosure. That is, the processors 1510 may perform operations/methods according to various embodiments of the present disclosure by executing one or more instructions.

For example, the computer program 1560 may include instructions for receiving the medical image and outputting the indices of biomarker expression for the at least one lesion included in the medical image using the first machine learning model. In this case, the computer program 1560 may include instructions for extracting the regions for the at least one lesion from the received medical image and cropping the extracted regions for the at least one lesion from the medical image to generate the partial images. In addition, the computer program 1560 may include instructions for inputting the partial images to the first machine learning model to output the indices of biomarker expression for the at least one lesion. In addition, the computer program 1560 may include instructions for generating the medical image including the output indices of biomarker expression and outputting or displaying the generated image on the display device.

The above description of the present disclosure is provided to enable those skilled in the art to make or use the present disclosure. Various modifications of the present disclosure will be readily apparent to those skilled in the art, and the general principles defined herein may be applied to various modifications without departing from the spirit or scope of the present disclosure. Thus, the present disclosure is not intended to be limited to the examples described herein but is intended to be accorded the broadest scope consistent with the principles and novel features disclosed herein.

Although example implementations may refer to utilizing aspects of the presently disclosed subject matter in the context of one or more standalone computer systems, the subject matter is not so limited, and they may be implemented in conjunction with any computing environment, such as a network or distributed computing environment. Furthermore, aspects of the presently disclosed subject matter may be implemented in or across a plurality of processing chips or devices, and storage may be similarly influenced across a plurality of devices. Such devices may include PCs, network servers, and handheld devices.

Although the present disclosure has been described in connection with some embodiments herein, it should be understood that various modifications and changes can be made without departing from the scope of the present disclosure, which can be understood by those skilled in the art to which the present disclosure pertains. Further, such modifications and changes are intended to fall within the scope of the claims appended herein.

What is claimed is:

1. A method comprising:
    obtaining a medical image created by capturing at least one part of a patient's body without tissue collection; and
    using at least one processor:
        inputting the medical image to a machine learning model;
        outputting information related to a biomarker expression for each of a plurality of lesions in the medical image by using the machine learning model, wherein the plurality of lesions are detected in the medical image; and
        determining information associated with tissue collection for the plurality of lesions in the medical image based on the information related to the biomarker expression.

2. The method according to claim 1, wherein the outputting the information related to the biomarker expression comprises:
    extracting regions containing at least one of the plurality of lesions from the medical image; and
    cropping the regions to generate partial images.

3. The method according to claim 2, wherein the outputting the information related to the biomarker expression further comprises inputting the partial images to the machine learning model to output the information related to the biomarker expression.

4. The method according to claim 2, wherein the outputting the information related to the biomarker expression further comprises inputting the medical image and the partial images to the machine learning model to output the information related to the biomarker expression.

5. The method according to claim 2, further comprising:
    determining segmentation information of each of the plurality of lesions,
    wherein the outputting the information related to the biomarker expression comprises inputting the segmentation information and the partial images to the machine learning model to output the information related to the biomarker expression.

6. The method according to claim 2, further comprising:
    acquiring different information related to biomarker expression for a different lesion from the plurality of lesions,
    wherein the outputting the information related to the biomarker expression comprises inputting the different information related to the biomarker expression of the different lesion and the partial images to the machine learning model to output the information related to the biomarker expression.

7. The method according to claim 1,
    wherein the obtaining the medical image comprises obtaining a first medical image of at least one part of the patient's body and a second medical image of at least one part of the patient's body captured at different time points, and
    wherein the outputting the information related to the biomarker expression comprises:
        extracting regions for the plurality of lesions from each of the first medical image and the second medical image; and
        inputting the regions extracted from the first medical image and the regions extracted from the second medical image to the machine learning model to output the information related to the biomarker expression.

8. The method according to claim 1, wherein the information associated with the tissue collection includes at least one of: information on a method of the tissue collection, information on a location of the tissue collection, or a priority of the tissue collection.

9. The method according to claim 1, further comprising:
    outputting information on priorities of the tissue collection for each of the plurality of lesions.

10. The method according to claim 9, further comprising:
acquiring reference information on the tissue collection associated with the medical image,
wherein the outputting the information on the priorities of the tissue collection for each of the plurality of lesions comprises determining the priorities of the tissue collection for each of the plurality of lesions based on the information related to the biomarker expression and the reference information.

11. An information processing system comprising:
at least one memory storing one or more instructions; and
at least one processor connected to the at least one memory and configured to execute the one or more instructions to:
  obtain a medical image created by capturing at least one part of a patient's body without tissue collection,
  input the medical image to a machine learning model,
  output information related to a biomarker expression for each of a plurality of lesions by using the machine learning model, wherein the plurality of lesions are detected in the medical image, and
  determine information associated with tissue collection for the plurality of lesions in the medical image based on the information related to the biomarker expression.

12. The information processing system according to claim 11, wherein the at least one processor is further configured to execute the one or more instructions to:
  extract regions containing at least one of the plurality of lesions from the medical image; and
  crop the regions to generate partial images.

13. The information processing system according to claim 12, wherein the at least one processor is further configured to execute the one or more instructions to:
  input the partial images to the machine learning model to output the information related to the biomarker expression.

14. The information processing system according to claim 12, wherein the at least one processor is further configured to execute the one or more instructions to:
  input the medical image and the partial images to the machine learning model to output the information related to the biomarker expression.

15. The information processing system according to claim 12, wherein the at least one processor is further configured to execute the one or more instructions to:
  determine segmentation information of each of the plurality of lesions; and
  input the segmentation information and the partial images to the machine learning model to output the information related to the biomarker expression.

16. The information processing system according to claim 12, wherein the at least one processor is further configured to execute the one or more instructions to:
  acquire different information related to biomarker expression for a different lesion from the plurality of lesions; and
  input the different information related to the biomarker expression of the different lesion and the partial images to the machine learning model to output the information related to the biomarker expression.

17. The information processing system according to claim 11, wherein the at least one processor is further configured to execute the one or more instructions to:
  receive a first medical image of the patient's body and a second medical image of the patient's body captured at different time points;
  extract regions for the plurality of lesions from each of the first medical image and the second medical image; and
  input the regions extracted from the first medical image and the regions extracted from the second medical image to the machine learning model to output the information related to the biomarker expression.

18. The information processing system according to claim 11, wherein the information associated with the tissue collection includes at least one of: information on a method of the tissue collection, information on a location of the tissue collection, or a priority of the tissue collection.

19. The information processing system according to claim 11, wherein the at least one processor is further configured to execute the one or more instructions to:
  output information on priorities of the tissue collection for each of the plurality of lesions.

20. The information processing system according to claim 19, wherein the at least one processor is further configured to execute the one or more instructions to:
  acquire reference information on the tissue collection associated with the medical image; and
  determine the priorities of the tissue collection for each of the plurality of lesions based on the information related to the biomarker expression and the reference information.

* * * * *